(12) United States Patent
Sheu

(10) Patent No.: US 7,548,776 B2
(45) Date of Patent: Jun. 16, 2009

(54) METHOD AND SYSTEM FOR PERFORMING FEVER TRIAGE

(75) Inventor: Yih-Ran Sheu, Yung-Kang (TW)

(73) Assignee: Southern Taiwan University of Technology, Tainan County (TW)

( * ) Notice: Subject to any disclaimer, the term of this patent is extended or adjusted under 35 U.S.C. 154(b) by 855 days.

(21) Appl. No.: 11/052,234

(22) Filed: Feb. 8, 2005

(65) Prior Publication Data
US 2006/0178582 A1 Aug. 10, 2006

(51) Int. Cl.
*A61B 6/00* (2006.01)
(52) U.S. Cl. .................. 600/474; 600/476; 600/549
(58) Field of Classification Search ............. 600/474, 600/473, 475, 549, 300, 476; 250/332, 333; 374/208, 100, 124; 340/573.7; 380/154
See application file for complete search history.

(56) References Cited

U.S. PATENT DOCUMENTS 5,056,525 A * 10/1991 Hafezi .................. 600/474
5,712,482 A * 1/1998 Gaiser et al. ........... 250/363.08
6,496,594 B1 * 12/2002 Prokoski .................. 382/118
7,397,380 B1 * 7/2008 Smolsky ................. 340/573.1
2004/0208230 A1 * 10/2004 Lee et al. .................. 374/208

* cited by examiner

*Primary Examiner*—Eric F Winakur
*Assistant Examiner*—Lawrence N Laryea
(74) *Attorney, Agent, or Firm*—Muncy, Geissler, Olds & Lowe, PLLC

(57) ABSTRACT

A method and a system are disclosed for performing fever triage. At first, a thermal image-detecting unit is used to detect a testee at a time-point and a position so as to form thermal image data. Meanwhile, a visible light image-detecting unit is used to detect the testee at the same time-point and position so as to form visible light image data. Thereafter, thermal image data are analyzed to determine if at least one fever-temperature block thereof is within a predetermined temperature range. Then, the fever-temperature block is analyzed to determine if it is corresponding to the skin portions of the visible light image data. Thereafter, if the result of the previous step is yes, then a warning signal is issued to indicate that the testee has fever.

10 Claims, 3 Drawing Sheets

METHOD AND SYSTEM FOR PERFORMING FEVER TRIAGE

FIELD OF THE INVENTION

The present invention relates to a method and a system for performing fever triage, and more particularly, to the method and the system for performing fever triage by using an image processing skill with a thermal imager (or an infrared camera) and a visible light's camera.

BACKGROUND OF THE INVENTION

There are quite a lot of types for body thermometers, roughly including mercury thermometers, electronic thermometers, ear thermometers, forehead thermometers and further infrared cameras. While the thermometer types are different, the measurement methods and degrees of recognition thereof are also different accordingly. Mercury thermometers and electronic thermometers belong to contact-typed body thermometers, and have to closely contact human bodies for obtaining correct temperature, wherein the temperatures of main body portions to be measured are rectal temperature, axillary (under arm) temperature and oral temperature. The temperatures measured by direct contact have relatively higher accuracy, but the sensors used thereby have longer response time, and thus cannot be applied in a fever triage station that requires rapid temperature measurements.

Ear thermometers, forehead thermometers and Infrared cameras all belong to non-contact devices, which mainly use Infrared sensors to sense body surface temperature. Although these devices have the advantage of short measurement time, yet the body surface temperatures are varied in accordance with ambient air temperature, so that the values measured thereby need to be adjusted or modified. Although an ear thermometer has relatively higher accuracy, yet it takes some time to replace an ear cover and read temperature, and also there is latent risk with short distance contact while in measurement. In addition, the consummation of ear covers is also quite a waste of resource. Hence, the ear thermometer cannot tackle with the areas having heavy flow of people.

For achieving the goal of heavy-flow and rapid fever triage, only infrared cameras can be relied on. Therefore infrared cameras are installed on many large areas to measure body temperatures for performing fever triage. However, an infrared camera senses the temperature in its whole available area. Therefore, when a testee enters a room from outdoors, his hair, mask or darker clothes will dissipate more heat indoors due to more heat absorbed from sunshine on those parts, causing the infrared camera to make an erroneous fever decision for the testee because of the heat-dissipation problem occurring on those non-human body parts. Generally, the infrared camera needs to be operated in coordination with an observer for monitoring the fever spots, and the measurement process cannot be automatically operated. On the other hand, the observer staring at the screen to artificially exclude erroneous decisions is easily to get tired. Especially in the areas of heavy people flow, since the time for a testee to show up on the screen is quite short and thus the observer is easily to be tired, it is very likely to cause an erroneous decision for allowing a genuine fever patient to pass through.

Hence, there is an urgent need to develop a method and a system for performing fever triage, thereby automatically recognizing fever patients and avoiding making erroneous decisions.

SUMMARY OF THE INVENTION

In accordance with one aspect, the present invention is to provide a method and a system for performing fever triage, so as to rapidly and automatically triage fever patients and avoid making erroneous decisions.

According to the aforementioned aspect, a method and a system for performing fever triage are used for detecting the status of the body surface temperature of a testee at a time-point and a position.

According to an embodiment of the present invention, the method for performing fever triage comprises the steps of: detecting the testee at the time-point and the position with a thermal image-detecting unit, thereby obtaining thermal image data, wherein the thermal image data records the temperatures in accordance with the body parts of the testee; detecting the testee at the time-point and the position with a visible light image-detecting unit, thereby obtaining visible light image data; analyzing and determining if at least one fever-temperature block of the thermal image data is within a predetermined temperature range, thus obtaining a first result; analyzing and determining if the fever-temperature block is corresponding to the person's skin portions of the visible light image data when the first result is yes, thus obtaining a second result; and issuing a warning signal indicating that the testee has fever when the second result is yes.

According to the embodiment of the present invention, the system for performing fever triage comprises: a thermal image-detecting unit used for collecting and converting the body surface temperature of the testee to thermal image data; a visible light image-detecting unit (such as a CCD (Charged-Coupled Device) or CMOS camera) used for collecting visible light image data of the testee; a processing unit connected to said thermal image-detecting unit and said visible light image-detecting unit, wherein the processing unit is used for analyzing and comparing the thermal image data with the visible light image data so as to determine if the testee has fever; and a display unit used for showing the analysis result made by the processing unit.

Hence, with the application of the present invention, fever patients can be rapidly and automatically triaged, and the chance for making erroneous decisions regarding fever cases can be effectively reduced.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is featured in using a thermal image-detecting unit and a visible light image-detecting unit to detect a testee respectively so as to collect thermal image data and visible light image data, and then in using an image processing method to compare the thermal image data with the visible light image data to see if fever-temperature block of the thermal image data is corresponding to (resides in) the person's skin portions of the visible light image data, thereby determining if the testee has fever. The thermal image-detecting unit can be such as an infrared camera, etc., and the visible light image-detecting unit can be such as a CCD camera, a CMOS camera or any other cameras within visible light range.

Figure 2:
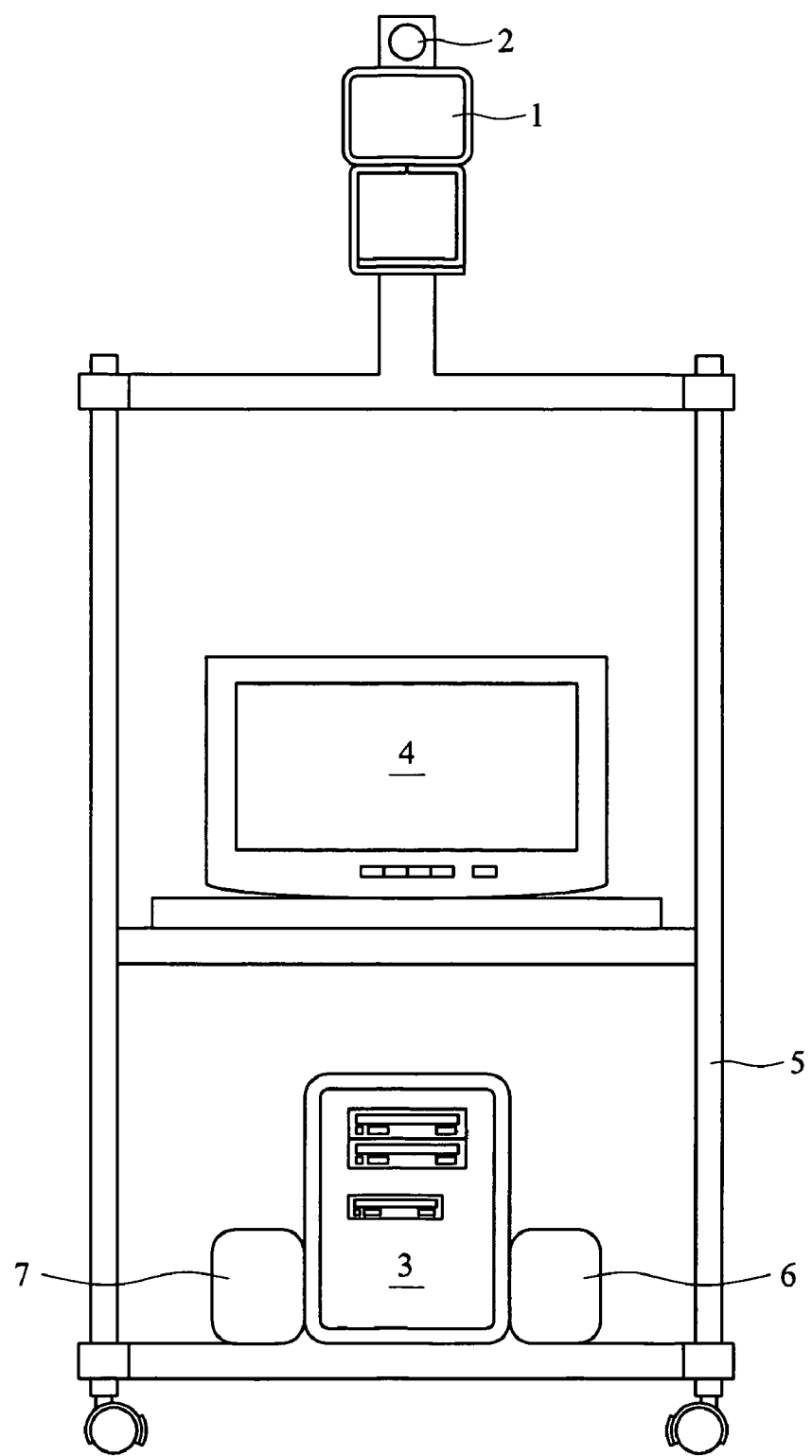
FIG. 2 is a schematic diagram showing a system for fever triage according to the embodiment of the present invention.

Referring to FIG. 2, FIG. 2 is a schematic diagram showing a system for fever triage according to an embodiment of the present invention. The system of the present invention for fever triage includes a thermal image-detecting unit 1, a visible light image-detecting unit 2, a processing unit 3 and a display unit 4, and all the aforementioned components can be mounted on a utility cart 5 for being conveniently moved. The components can also be mounted on a fixed base. The thermal image-detecting unit 1 is used for continuously collecting body surface temperatures of a testee, and also converting those body surface temperatures to thermal image data. The visible light image-detecting unit 2 is used for continuously collecting visible light image data of the testee, wherein the visible light image data and the thermal image data both are taken at the same position and the same time-point. The processing unit 3 (such as a computer) is connected to the thermal image-detecting unit 1 and the visible light image-detecting unit 2, and is used for analyzing and comparing the thermal image data with the visible light image data so as to determine if the testee has fever. The display unit 4 (such as a screen) is used for showing the analysis result made by the processing unit 3. Further, the processing unit 3 can be equipped with a warning device 6 used for issuing a warning signal, and with an audio unit 7 (such as a speaker) used for sending voice information.

The detailed skills for implementing the thermal image-detecting unit 1, the visible light image-detecting unit 2 and the processing unit 3 are all know to those who are skilled in the art, and are not the main points of the present invention, and thus are not described herein.

To set up the system of the present invention for fever triage, a thermal image-detecting unit 1 and visible light image-detecting unit 2 are first fixed on two relative positions in such as a utility cart 5, and a marker is placed in front of the thermal image-detecting unit 1 and the visible light image-detecting unit 2 with a proper distance. The marker is used for adjusting the coordinate relationship between two respective images formed by the thermal image-detecting unit 1 and the visible light image-detecting unit 2, thereby adjusting the coordinate relationship between thermal image data and visible light image data in the subsequent steps. It is noted that this coordinate-adjusting step merely needs to be performed once.

For obtaining better efficacy, the focal length of the lens of the visible light image-detecting unit 2 can be made to meet the visible range of the thermal image-detecting unit 1, so that the conversion formula used in the coordinate-adjusting step can be purely a coordinate translation. However, the present invention is not limited thereto.

Figure 1:
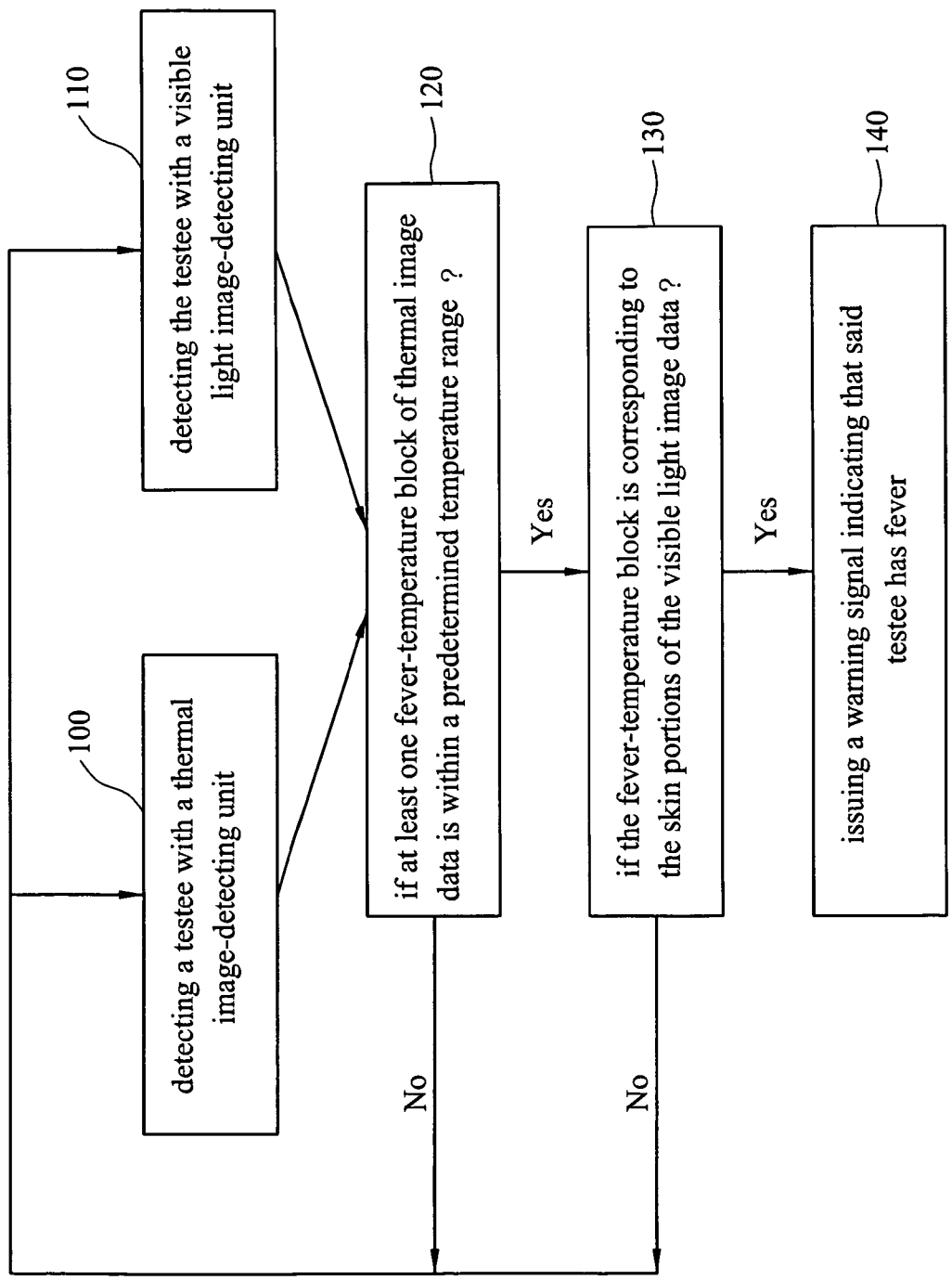
FIG. 1 is a schematic flow chart showing a method for fever triage according to an embodiment of the present invention.

Referring to FIG. 1 and FIG. 2, FIG. 1 is a schematic flow chart showing a method for fever triage according to an embodiment of the present invention. At first, step 100 is performed for detecting a testee with a thermal image-detecting unit 1, and thus thermal image data are obtained, wherein the thermal image data record the temperatures in accordance with the body parts of the testee. Meanwhile, step 110 is performed for detecting the testee with a visible light image-detecting unit at the same time (time-point) and same position with the thermal image-detecting unit 1, and thus visible light image data is obtained.

Figure 3:
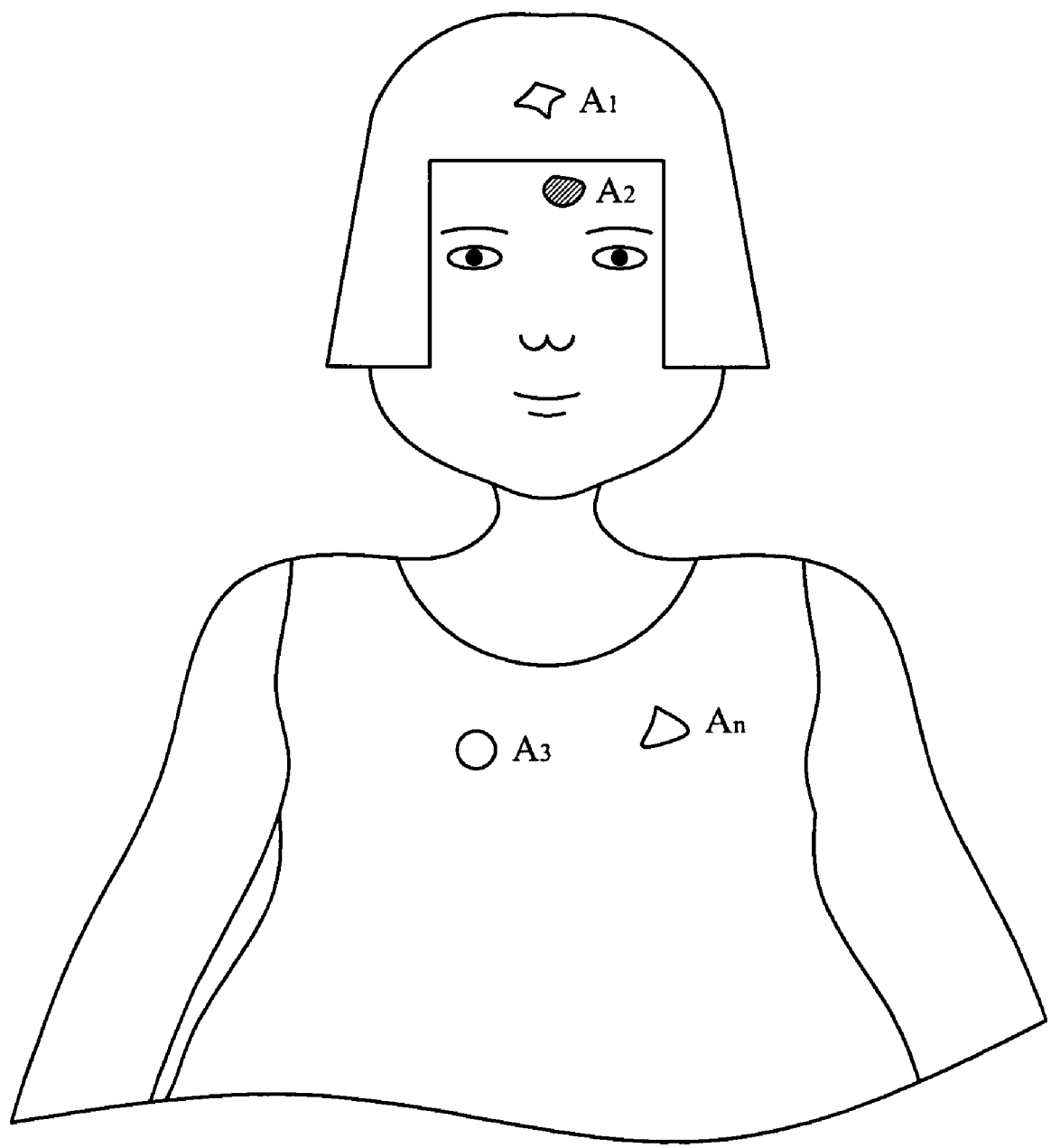
FIG. 3 is a schematic diagram showing a thermal image formed by thermal image data.

Thereafter, step 120 is performed to determine if at least one "fever"-temperature block of the thermal image data is within a predetermined range, i.e. if the fever-temperature block is greater than a first predetermined temperature and smaller than a second predetermined temperature, wherein the first predetermined temperature is the lowest fever temperature, such as 37.5 degrees Celsius, and the second predetermined temperature is the highest temperature that human skin temperature can reach, such as 42 degrees Celsius, which is generally beyond a walker's maximum skin temperature. For saving computation time, the fever-temperature block may be merely limited to being greater than the first predetermined temperature. Referring to FIG. 3, FIG. 3 is a schematic diagram showing a thermal image formed by thermal image data. On the thermal image, there are several fever-temperature blocks $A_1, A_2, A_3 \ldots A_n$. For easy discrimination, different color (such as orange red) can be labeled on the fever-temperature blocks $A_1, A_2, A_3 \ldots A_n$. If no fever-temperature block is found, then step 100 and step 110 are performed again.

If at least one fever-temperature blocks (such as $A_1, A_2, A_3 \ldots A_n$) are found, then step 130 is performed to determine if the fever-temperature blocks $A_1, A_2, A_3 \ldots A_n$ are corresponding to the person's skin portions of the visible light image data. If any fever-temperature block (such as $A_2$) belongs to the person's skin portions (such as forehead) of the visible light image data, then step 140 is performed for issuing a warning signal indicating that the testee has fever. If no fever-temperature blocks belong to any person's skin portions, then step 100 and step 110 are performed again.

As to the method for determining if the fever-temperature blocks $A_1, A_2, A_3 \ldots A_n$ belong to person's skin portions, several methods can be applied. The original visible light image data are generally taken in RGB (Red-Green-Blue) mode. Since the RGB mode is easily to be affected by light, the original visible light image data are first converted to YIQ, YUV or HSV mode, and then are searched for skin color portions via chrominance coordinates (IQ, UV or HS). For avoiding the confusion of the locations of the skin color portions, several feature comparison methods can be performed to check whether the skin color portions are located on the body parts of the testee, particularly on the face part of the testee. For example, an oval comparison method can be used to determine if the skin color portions belong to the features of the testee's face. The above description is merely stated for explaining the enablement of the present invention, and any image-processing skills can also used in the present invention. Further, the related image-processing skills are not the main points of the present invention, and thus are not described herein.

Hence, it can be known from the aforementioned embodiment that the present invention is featured in using image processing skills to determine if the fever-temperature portions of the testee belong to the skin portions of human body, thereby avoiding erroneous decisions of fever cases without having an observer for monitoring, thus achieving the efficacy of rapidity and automation.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure.

What is claimed is:

1. A method for performing fever triage, comprising:
   detecting a testee at a time-point and a position with a thermal image-detecting unit, thereby obtaining thermal image data, wherein said thermal image data record a plurality of temperatures in accordance with a plurality of body parts of said testee;
   detecting said testee at said time-point and said position with a visible light image-detecting unit, thereby obtaining visible light image data showing a plurality of colors of said body parts;
   analyzing and determining at least one of said plurality of temperatures of said image data within a predetermined temperature range, thus obtaining a first result, thereby defining said at least one of said plurality of temperatures of said thermal image data as at least one fever temperature block;
   locating at least one skin color portion on said visible light image data, wherein said at least one skin color portion represents at least one skin portion of said testee;
   analyzing and determining if said at least one fever-temperature block is corresponding to said at least one skin portion of said visible light image data;
   determining if said at least one skin portion corresponding to said at least one fever temperature block is of said plurality of temperatures is located on a selected body part of said testee by using at least one feature comparison method, thus obtaining a second result; and
   issuing a warning signal indicating that said testee has a fever when said second result is yes.

2. The method for performing fever triage according to claim 1, further comprising:
   returning to said step of detecting said testee at said time-point with said thermal image-detecting unit when said first result is no.

3. The method for performing fever triage according to claim 1, wherein said selected body part is said testee's face, and said feature comparison method comprises an oval comparison method.

4. A system for performing fever triage, used for detecting the status of a body surface temperature of a testee at a time-point and a position, wherein said system for performing fever triage comprises:
   a thermal image-detecting unit used for collecting and converting a plurality of body surface temperatures of said testee to thermal image data;
   a visible light image-detecting unit used for collecting visible light image data of said testee;
   a processing unit connected to said thermal image-detecting unit and said visible light image-detecting unit, wherein said processing unit is configured to execute the step of determining if at least one of said plurality of temperatures of said thermal image data within a predetermined temperature range thus obtaining a first result, wherein said at least of said plurality of temperatures of said thermal image data is defined as at least one fever temperature block;
   said processing unit is configured to execute the step of determining if said at least one fever-temperature block is corresponding to at least one skin portion of said visible light image data; and
   said processing unit is configured to execute the step of determining if said at least one skin portion corresponding to said at least one fever-temperature block is located on a selected body part of said testee by using at least feature comparison method so as to determine if said testee has a fever; and
   a display unit used for showing the analysis result made by said processing unit.

5. The system for performing fever triage according to claim 4, wherein said thermal image-detecting unit is an Infrared thermal imager.

6. The system for performing fever triage according to claim 4, wherein said visible light image-detecting unit is a camera.

7. The system for performing fever triage according to claim 4, wherein said processing unit is equipped with a warning device for issuing a warning signal.

8. The system for performing fever triage according to claim 4, wherein said processing unit is equipped with an audio unit for sending voice information.

9. The system for performing fever triage according to claim 4, wherein said thermal image-detecting unit, said visible light image-detecting unit and said processing unit are mounted on a utility cart or on a fixed base.

10. The system for performing fever triage according to claim 4, wherein said selected body part is said testee's face, and said feature comparison method comprises an oval comparison method.

* * * * *